US009126038B2

(12) United States Patent  
Barbero Castro (10) Patent No.: US 9,126,038 B2
(45) Date of Patent: Sep. 8, 2015

(54) SYSTEM FOR STIMULATING HAIR GROWTH (75) Inventor: Narciso Barbero Castro, Barcelona (ES)

(73) Assignee: Roel Electrocosmetics, S.C.P., Barcelona (ES)

(*) Notice: Subject to any disclaimer, the term of this patent is extended or adjusted under 35 U.S.C. 154(b) by 0 days.

(21) Appl. No.: 14/237,644

(22) PCT Filed: Aug. 9, 2012

(86) PCT No.: PCT/ES2012/070621
§ 371 (c)(1),
(2), (4) Date: Feb. 7, 2014

(87) PCT Pub. No.: WO2013/021092
PCT Pub. Date: Feb. 14, 2013

(65) Prior Publication Data
US 2014/0194966 A1 Jul. 10, 2014

(30) Foreign Application Priority Data
Aug. 10, 2011 (ES) .................................. 201131377

(51) Int. Cl.
A61N 1/00 (2006.01)
A61N 1/32 (2006.01)
A61N 1/40 (2006.01)

(52) U.S. Cl.
CPC . *A61N 1/326* (2013.01); *A61N 1/40* (2013.01)

(58) Field of Classification Search
CPC ....................................................... A61N 1/32
USPC ........................................ 607/115, 145, 154
See application file for complete search history.

(56) References Cited

U.S. PATENT DOCUMENTS

2005/0251242 A1* 11/2005 Bousfield et al. ............. 607/150

FOREIGN PATENT DOCUMENTS

| ES | 8704742 | 7/1987 |
| ES | 2278499 | 8/2007 |
| GB | 154535 | 2/1922 |
| JP | 2009247526 | 10/2009 |
| MX | PA05009107 | 12/2005 |
| WO | 9526781 | 10/1995 |

* cited by examiner

Primary Examiner — Nicole F Lavert
Assistant Examiner — Nadia A Mahmood
(74) Attorney, Agent, or Firm — Davis & Bujold, P.L.L.C.; Michael J. Bujold (57) ABSTRACT The invention relates to a system (1) for stimulating hair growth in a pre-determined area of skin, comprising: means (31) for generating high-voltage alternating current, means (35, 36) for generating a variable electric field from the high-voltage alternating current generated, and means (11) for applying the generated variable electric field to a pre-determined area of skin. In addition, the means for generating a variable electric field include at least two radiating elements (35, 36), while the means for generating high-voltage alternating current include a transformer (31), the primary of said transformer being disposed in relation to the core in such a way that, during operation, the radiating elements (35, 36) generate a variable electric field with a radiation pattern that concentrates its energy close to the means (11) for applying the variable electric field.

13 Claims, 4 Drawing Sheets

SYSTEM FOR STIMULATING HAIR GROWTH

The present invention relates to a system for stimulating hair growth in a pre-determined area of skin through the generation of variable electric fields from high-voltage alternating current.

STATE OF THE ART

As described in Spanish patent ES 2278499 B1, titled "Dispositivo para generar electroósmosis" (Device for generating electro-osmosis", it is known in the state of the art the so-called osmosis phenomenon, which is based on ions or suspended particles separated by a porous or semi-pervious membrane that can fully traverse said membrane. This phenomenon can be enhanced and accelerated by applying a major electric field, this phenomenon being then referred to as electro-osmosis.

In case that the electric field applied to achieve said acceleration exhibits an alternating polarity and depending on the frequency with which said alternation occurs, it is possible to achieve conveyance of the particles to a particular location to the user's convenience, this phenomenon being then referred to as dielectrophoresis.

A feature that is common to all the above-described phenomena is that temperature becomes an enhancing effect of the translational movement of the particles all across the membrane.

The equipments for applying electro-osmosis and dielectrophoresis comprise high voltage generators, generating either AC or DC voltage. Such high voltage is conveyed by some cables to some generally metallic plates which jointly create an electric field.

It is also disclosed in the aforementioned patent that the membrane on which electro-osmosis occurs can be skin (for instance human skin) and that, depending on the electric field generated and applied thereon, a heating process caused by dielectric losses on both sides of the skin may occur, this process being controllable and notably capable of accelerating the osmotic effect, thereby increasing speed and the amount of conveyed ions or particles.

Apart from the osmotic effect obtained thanks to the device (an effect that can also be applied), several researches have suggested that the heating process yielded by the device on the skin from specific values of the electric field that is generated may become suitable to stimulate hair growth in the area on which it is applied.

The main drawback associated with the use of the device described and claimed in the aforesaid patent is that the radiation pattern related to the electric field generated in the applicator of the device exhibits high energy values even at sufficiently deep spots of the skin, which may even affect the patient's health. Thus, for instance, use of the device for stimulating hair growth (i.e., if it is applied on the scalp) may result in high energies reaching depths located beyond the skull, which could cause more or less serious damage to the patient's brain.

EXPLANATION OF THE INVENTION

It is therefore an object of the invention to provide a system for stimulating hair growth that overcomes the above-described drawbacks.

The above object is achieved in accordance with claim 1 by providing a system for stimulating hair growth in a pre-determined area of skin comprising means for generating high-voltage alternating current; means for generating a variable electric field from the high-voltage alternating current so generated; and means for applying the so generated variable electric field on the pre-determined area of skin; the means for generating a variable electric field comprising at least two radiating elements; and the means for generating high-voltage alternating current comprising a transformer, whose primary is disposed in relation to the core in such a way that, during operation, the radiating elements generate a variable electric field with a radiation pattern that concentrates its energy in the proximity of the means for applying the variable electric field.

Depending on the arrangement of the primary in relation to the core, it is possible to control the coverage of the radiation pattern, that is to say, if the coupling position (primary of the transformer) in relation to the core is modified, it is then obtained a modification of the amplitude of the variable electric field generated by the radiating elements, it being then possible to adjust the effective scope of the radiation pattern. Obviously, this arrangement of the coupling in relation to the core intended to make the radiation pattern suitable for using the system of the invention to stimulate hair growth depends on, among other things, the location of the area of skin to be treated (i.e., the radiation pattern could be different should the system be applied on scalp or on another body region) and the configuration of the system itself, for instance, the type of transformer (i.e. it can depend on, among other things, the number of turns of the coupling or the values of the components of the resonant circuit).

The fact that it is achieved that the radiation pattern concentrates its energy in the proximity of the means for applying the variable electric field results in a slight heating (through the action of the ionic movement caused on the tissue) of the skin (of the scalp in case that it is intended to stimulate hair growth), although only of the skin structure where the pilosebaceous follicles are located. This heating causes vasodilatation, an increase in the blood flow and stimulation of the cellular respiratory processes such that the kerotinocytes forming the hair undergo an increase in cellular respiration through the mitochondria, thus increasing the energy level that favors hair growth. The stabilization of the hair structures (or the hair in general) results in an improvement in the cellular metabolism and the ordered growth of the tissue.

Additionally, it is also achieved both the permeation of the skin and the above-described electro-osmotic effect, which makes it suitable for simultaneously working with drugs or cosmetics formulated to nourish or repair hair deficiencies since they are driven to penetrate during treatment with the system of the invention.

On the other hand, the fact that the radiation pattern concentrates its energy in the proximity of the means for applying the variable electric field (for instance, on its outer surface) means that this radiation pattern is deprived of significant energy beyond the skin surface (or the skull surface, if the system is applied on the scalp with the purpose of stimulating hair growth), such that no damage is inflicted on the patient.

The means for generating high-voltage alternating current can preferably generate high-voltage alternating current from low-voltage alternating current (i.e. the transformer is a step up transformer), and the system may also comprise means for generating low-voltage alternating current, and means for transporting the low-voltage alternating current so generated to the means for generating high-voltage alternating current.

The means for generating low-voltage alternating current can be arranged spaced apart (for instance in several containers) or together (for instance in the same container) along with the remaining means described above (then understandably forming a radiating applicator). In case that the aforesaid means of transport are spaced apart, they can be, for instance, electric cables, whereas if the means are arranged together, the means of transport can be, for instance, conductive tracks of a printed circuit board.

As described above, it may be suitable that the means for generating high-voltage alternating current and the means for applying the electric field so generated be arranged together, such that the high-voltage alternating current and the electric field can be generated at the same spot where the electric field is applied on the skin. In this way, it is prevented the transfer of high voltage and it becomes unnecessary for the means delivering the low-voltage alternating current generated to the means for generating high-voltage alternating current to be special cables inasmuch as the alternating current delivered is of a low-voltage nature. Moreover, it is thus avoided any shock hazards or burns affecting the users and the operating frequency of the system does not become altered by the presence of bodies in the proximity or in contact with the cable. The operating frequency does not become altered by other features such as cable length or winding thereof either. This all being due to the fact that the transmission of low-voltage alternating current is carried out at low impedance.

In accordance with a preferred embodiment of the invention, the transformer is a resonant transformer and, depending on the location on the body of the pre-determined area of skin, the core is disposed in relation to the resonant circuit so that, during operation, the resonant circuit is in tune.

The resonant transformer comprises a resonant circuit that may be made up of an inductance and a condenser to which it can be coupled, in an inductive, capacitative or direct fashion, the signal coming from the means for generating low-voltage alternating current. Through inductive coupling it is accomplished a great insulation between the resonant transformer and the remaining elements of the system.

On the other hand, when the radiating applicator rests on the body a tune change occurs caused by the change of capacitance of the resonant transformer circuit, this being regulated through the feedback in the generator that changes then its frequency to become tuned and thus maintain its output performance. This change in tune depends to a large extent on the pressure exerted on the tissue on which it rests, on the softness of the tissue, which when adapted, covers a larger contact area, and on the impedance of the tissue in question.

In case of resting the applicator on the skull, as it is hard it does not cave in, and besides, since the skull mostly lacks water and fat, it barely loads the output resonant circuit and as a result correction is hardly required.

Preferably, the means for applying the variable electric field are adapted to move about the entire pre-determined area of skin such that the same radiation pattern is applied on each of the spots of this pre-determined area of skin.

This adaptation of the means for applying the variable electric field to move about the entire pre-determined area of skin may be embodied in two configurations that are described below.

In accordance with an embodiment of the invention, the means for applying the variable electric field comprise a head, on which the means for generating a variable electric field are disposed, and a handle, on which the means for generating high-tension alternating current are disposed. It is understood that the above configuration defines a hand-held radiating applicator of the variable electric field.

In this way, the user of the system o another person can grab the radiating applicator by the handle described above and apply the radiation pattern of the variable electric field on the area on which hair growth is wished to be stimulated. Obviously, there takes place a uniform application of the variable electric field on each of the spots of the area of skin to be treated (for instance the human scalp) because the distance between the applicator (more specifically the head) and the skin is always the same (particularly if the stimulation is made through contact between the head of the applicator and the skin). That is, each one of the skin spots to be treated receives the same radiation pattern from the applicator.

Alternatively, the means for applying the variable electric field comprise a head, provided with means for generating a variable electric field, a housing for the means for generating high-voltage alternating current, and a mechanical system capable of moving at least the head across the entire pre-determined area of skin. This configuration is intended to comprise an "automatic" radiating applicator of variable electric fields.

Again, with this configuration of the radiating applicator it is accomplished a uniform application of the radiation pattern generated by the system on each of the skin spots to be treated, although it is in this case the system itself that, through a mechanical system, causes the automatic movement of the head across the entire area of skin to be treated. It is likely because of that that this configuration can be slightly more precise as far as the application of the radiation pattern is concerned than the configuration described above, when taking into account possible human errors, both as regards precision (i.e., keeping at all times the distance between the head of the applicator and the skin to be treated) and as regards reliability (i.e., the entire area of pre-determined skin is to be treated and no portions should be left untreated).

In accordance with a preferred embodiment of the invention, the radiating elements can be conductive tracks on a printed circuit board, the printed circuit board optionally being made of a flexible material. In this way, a board (and the conductive tracks in the form of radiating elements contained therein) can adopt multiple shapes and become adapted to the different surfaces of the head in which they are accommodated. Basically, the shape of each head may depend on the application for which it has been created. Thus, a head intended to be applied on the scalp can present a configuration different from that of a head intended to be applied on any other body region. In any case, the printed circuit board can be attached to the head.

The head of any of the configurations described above may comprise an element made of an insulating material in order to avoid both direct contact between the radiating elements and the skin and, as a result, the propagation of electric current across the skin.

The system operates at a frequency of between 100 KHz and 600 MHz. As disclosed above, the operating frequency mainly depends on the area of skin on which the system is applied to stimulate hair growth in accordance with the invention. Hence, if it is intended to stimulate hair growth (i.e., the system is applied on the scalp) the operation frequency can be of 480 KHz, whereas, if the system is applied on any other body region the operation frequency can be of 430 KHz. It is worth noting that the system would approximately operate in the same way at any of the frequencies indicated in the aforesaid interval. It is to be noted that the higher the operating frequency is, the more difficult penetration of the radiation pattern through the skin is, although that is not a problem because the invention is intended to operated on a superficial level. However, at low working frequencies fewer technical problems arise and the components to be used (for instance, semi-conductors and transmission cables) are far cheaper, this practical reason being why the operating frequencies indicated above (430 and 480 KHz) have been selected.

In accordance with another embodiment of the invention, the system may comprise means for insulating the system from the power supply, these means being optionally selected from at least one of the following elements:
The input transformer to the power system
The output RF transformer of the portion of low-voltage alternating current generated; and
the input RF transformer of the radiating applicator.

It is thus accomplished a suitable insulation of the system (more specifically of the radiating applicator) that guarantees the absence of leakage currents which may affect the body of the patient being treated.

The system may also comprise an element for indicating operation of the system, which can be a red light emitting diode (LED) having a wavelength of approximately 630 nm. The use and the suitable placement of a LED of this type in the radiating applicator, apart from signaling whether or not the system is in operation, also permits biostimulating the skin and thus an improvement of its appearance.

Other objects, advantages and features of the embodiments of the invention will become apparent for a person skilled in the art from the following description or can be learnt by performing the invention.

BRIEF DESCRIPTION OF THE DRAWINGS

Following is a description of specific embodiments of the present invention by way of non-limiting examples with reference to the accompanying drawings, wherein.

DETAILED EXPLANATION OF SOME EMBODIMENTS

Following is a description of a possible preferred embodiment of the system for stimulating hair growth in a pre-determined area of skin, this pre-determined area of skin corresponding to the scalp of a human being and, the system thus being used to stimulate hair growth.

Figure 1:
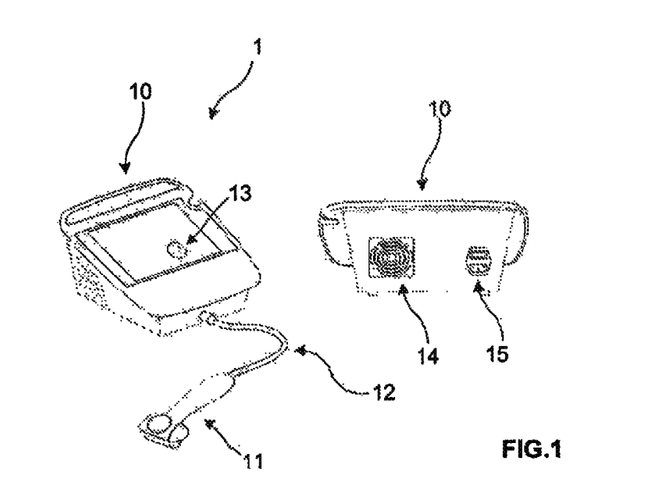
FIG. 1 is a schematic diagram of the system for stimulating hair growth in accordance with the invention.

As can be seen in FIG. 1, the system for stimulating hair growth comprises two perfectly distinct stages. Firstly, the entire stage for generating low-voltage alternating current is housed in a first casing 10, while in a second casing 11 in the form of a radiating applicator it is housed the entire of the stage for both generating high-voltage alternating current from low-voltage alternating current generated in the first stage 10 and for generating a variable electric field from the high-voltage alternating current so generated. The low-voltage alternating current is delivered from the stage 10 generating the low-voltage alternating current to the stage 11 generating the high-voltage alternating current through suitable electric cables 12. The fact that the high-voltage alternating current is generated at the same spot of application of the electric field and needs not be transported provides some important advantages:

It is not necessary to use special cables because what is being delivered is low-voltage alternating current;

Any possible shock hazards or burns affecting patients or users of the system are avoided;

The operating frequency of the system is not disrupted by any nearby object to the cable or any object in contact with it; or The frequency is not disrupted by other features such as the length of the electric cables or the winding thereof either.

As can be seen in the figure, the first stage 10 comprises, among other elements, a regulator 13 for the output level of the low-voltage alternating current generated; a fan 14 for cooling the electronics present in the first stage 10; and a connector 15 that permits connection of the stage to the power supply by means of a suitable electric cable.

In this figure it is also shown that the applicator 11 comprises a head for the application of the radiation pattern on the scalp to be treated and a handle so that the very patient or another person can be capable of moving the radiating applicator 11 across the entire scalp or a pre-determined area of same. With said configuration it is possible to ensure that the radiation pattern is applied in an uniform fashion across the entire scalp, particularly so if treatment of the area is conducted through contact between the scalp and the head of the radiating applicator 11.

Obviously, the radiating applicator 11 can exhibit different configurations. Thus, for instance, the radiating applicator 11 can also comprise a mechanical system capable of moving at least the head across the entire pre-determined area of skin. This configuration is understood to give shape to an "automatic" radiating applicator. In this case, it is also accomplished a uniform application of the radiation pattern generated by the system on each of the spots of the area of skin to be treated, although in this case it is the system itself, through the mechanical system, that causes the automatic movement of the head across the entire area of skin to be treated and ensures keeping the head either in contact with the skin or at a suitable pre-determined distance.

Figure 2:
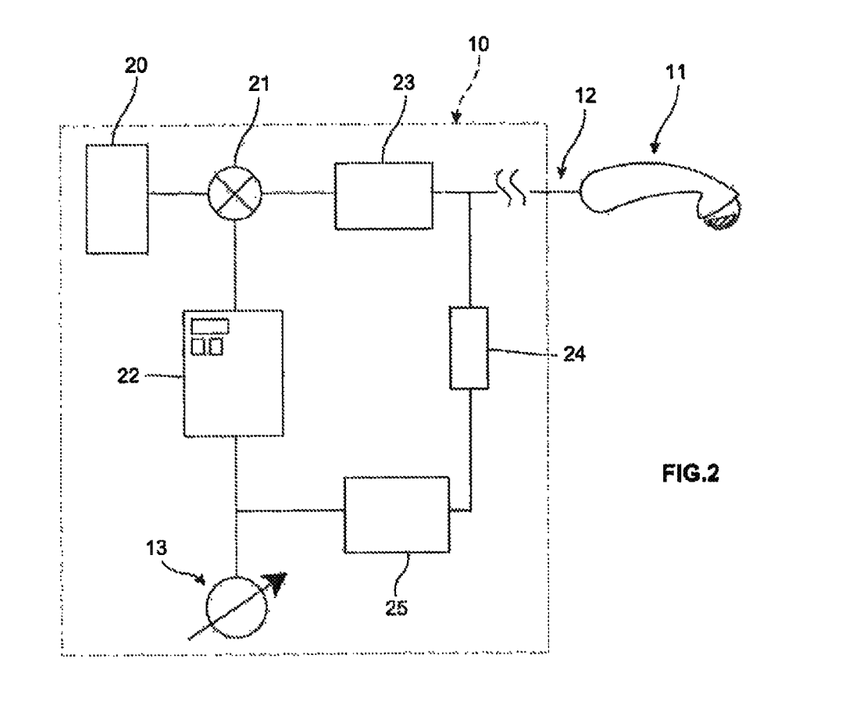
FIG. 2 is block diagram of the system for stimulating hair growth shown in FIG. 1.

More specifically, FIG. 2 shows a block diagram of the stage 10 generating low-voltage alternating current. As can be seen in this figure, this first stage 10 comprises an oscillating circuit 20 that generates the frequency required for operation purposes, it being thus obtained at its output a low-level continuous carrier; the circuit 13 for controlling the output level of the low-voltage alternating current that generates a square wave which alternates its timing between "1" and "0" depending on the manual control exerted by the user in order to obtain the desired amount of energy at the end of the radiating circuit; a modulator circuit 21 in charge of chopping the oscillator carrier 20 in accordance with the variable signal from the control 13; a circuit 22 for time control, i.e., a timer; an amplifying circuit 23 that receives the signal from the modulator 21 (this signal having no power whatsoever) and increases the power levels required for the desired application (a radio frequency transformer at the output of the amplifier 23 makes the signal conditional on the transmission line 12, which exhibits very low impedance and low voltage); a phase control circuit 24 (feedback) that keeps the output level stable and provides a slight variation in the operating frequency for permitting the output resonant circuit to maintain an optimal operating performance; and a circuit 25 for indicating the output level of the low-voltage alternating current signal. As disclosed above, the radiating applicator 11 receives the low-voltage alternating signal through the electric cables 12 (transmission line).

The signal from the power supply received by the stage of generation 10 of low-voltage alternating current is only used to feed the different circuits referred to above.

Figure 3:
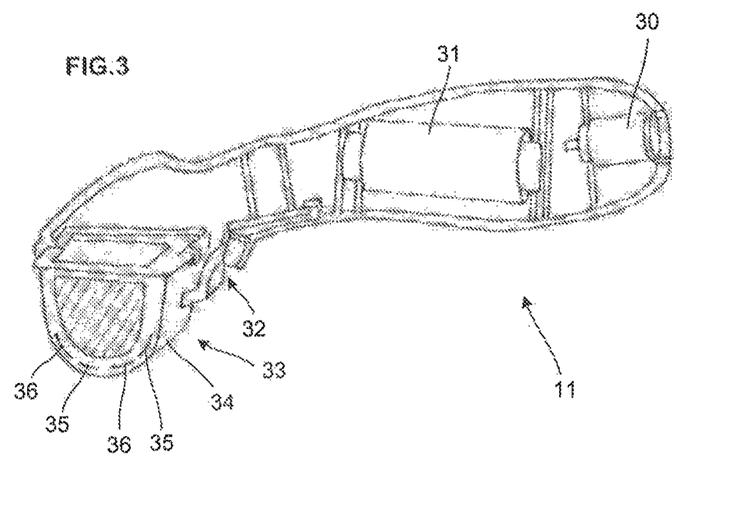
FIG. 3 is a schematic diagram of a longitudinal section of the radiating applicator element that is part of the system for stimulating hair growth shown in FIGS. 1 and 2.

On the other hand, also more specifically, FIG. 3 shows a longitudinal section of the radiating applicator 11, i.e., of the second stage of the system. Basically, the radiating applicator 11 comprises an input connector 30 to which electric cables 12 originating from the stage of generation 10 of low-voltage alternating current are connected; a resonant transformer 31 for generating a high-voltage alternating current signal from the low-voltage alternating current signal originating from the low-voltage stage 10; a light emitting diode 32 intended to indicate operation or inaction of the system; a head 33 from which it is applied the radiation pattern on the scalp area to be treated, this head comprising an insulation element 34 on which it is attached a printed circuit board made of a flexible material that houses two conductive tracks 35, 36 acting as radiating elements of the electric field (i.e., from said conductive tracks it is generated the radiation pattern).

It is to be noted that the applicator 11 can be alternated with other applicators that can exhibit different shapes and configurations suitable for the area on which they are to act and/or the application for which they are intended. Since the voltage attained by the applicator is low, it is possible to merely alternate the applicators without the cables, with no ensuing discharges suffered by the user doing so.

The fact that the head 33 comprises element 34 made of an insulating material represents an improvement to the insulation between the radiating applicator 11 in general and the patient, inasmuch as it is avoided both direct contact between the radiating elements 35, 36 and the skin and, hence, propagation of electric currents through the latter.

The light emitting diode 32 emits red light and exhibits a wavelength of 630 nm, which makes it suitable for, apart from indicating operation of inaction of the system, cosmetically treating the scalp. This chromatic wavelength has been long considered effective for cosmetic treatments, such as those destined to rejuvenate the skin. Basically, this wavelength stimulates the proliferation of fibroblasts, a skin cell that is essential for synthesizing collagen and elastin.

As an alternative to the light emitting diode, it could be possible to use a laser diode capable of also operating at the aforesaid wavelength.

Figure 4:
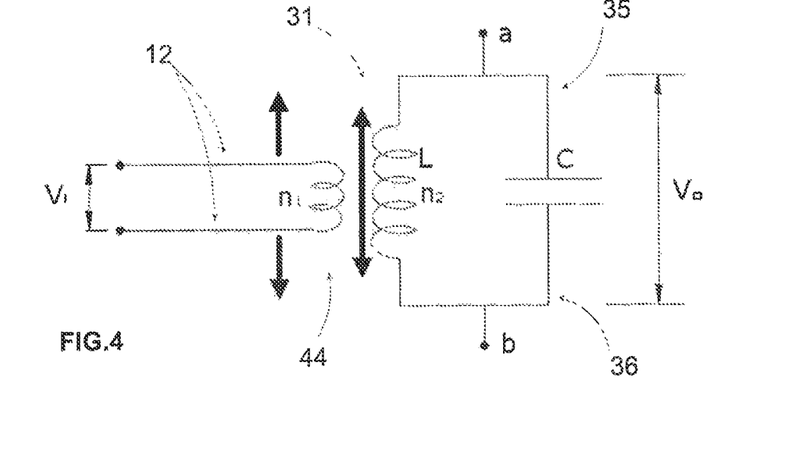
FIG. 4 shows a drawing of the electronics of the radiating applicator element shown in FIG. 3.

The configuration of the resonant RF transformer 31 will be explained below on the basis of FIG. 4.
The figure references represent:
$n_1$: number of turns of the coupling 44;
$n_2$: number of turns of inductance L;
L and C: the inductance and the condenser respectively forming the resonant circuit at a particular F frequency;
$V_i$: input voltage originating from the stage of generation 10 of low-voltage alternating current;
$V_o$: induced output voltage at the resonant circuit LC measured at its ends a and b.

Transformer 31 comprises an inductance L provided with $n_2$ turns and a condenser C to which it is inductively coupled 44 signal $V_i$ originating from the stage of generation 10 of low-voltage alternating current. Said coupling provides great insulation between the transformer 31 and the rest of the system 1. It should be noted that said coupling could also be performed, for instance, either in a capacitive way or in a direct way.

It is also to be noted that voltage $V_i$ generated at the stage of generation 10 of low-voltage alternating current can be variable as regards amplitude and frequency, and it can be modulated as well.

Resonant frequency F of the resonant circuit (transformer+radiating elements) is determined by the formula:

$$F = 1/6.28\sqrt{LC}$$

where F corresponds to the resonant frequency, L corresponds to the inductance (in Henrys) and C corresponds to the capacitance value (in Farads), as disclosed above.

The relation of the input voltage transformation with respect to the output voltage transformation is determined by the following formula:

$$V_o = (n_2/n_1)^2 V_i$$

The impedances of the inductance and the condenser must be the same ($Z_L = Z_C$), this situation only occurring in the resonant frequency F of the circuit, $Z_L$ being the impedance of the inductance that corresponds to $6.28 LF_o$, and $Z_c$ being the impedance of the condenser that corresponds to $1/(6.28 CF_o)$.

As can be seen in the same figure, conductive boards 35,36 are positioned at the ends of the resonant circuit as parts thereof (i.e. the radiating elements) for generating an electric field between them. Since the applied voltage is alternating as regards polarity, the field generated will also be alternating accordingly, thereby changing the direction of the transformer frequency 30.

The electric field so generated between the two radiating elements 35, 36 on which tension $V_o$ is applied is inversely proportional to the square of the distance separating them. It is for this reason that the radiating applicator 11 is to be placed as close as possible to the scalp, even making contact with it. Between the radiating applicator 11 and the scalp a fine layer of a specific product can be placed, for instance, a cosmetic, that is intended to penetrate through the semi-pervious scalp membrane. This product can be applied in a liquid or a gelatinous form.

Depending on the arrangement of the coupling (i.e. of the transformer primary 31) with respect to the core, it is obtained a radiation pattern of the electric field generated that concentrates its energy in the proximity of the head 33 (for instance at the outer wall of the insulating element 34 that is part of the head 33). This radiation pattern can ultimately merely penetrate between approximately 0 and 5 mm and vanishes in a short period of time such that the subsequent residual radiation of the radiation area is very weak and, hence, radiation underneath the skull is far below the accepted values.

The radiation pattern described above, when applied on the scalp, causes an ionic movement in the skin resulting in a slight temperature rise of same, although only affecting the skin structure where the pilosebaceous follicles are located. This heating causes vasodilatation, an increase in the blood supply and a stimulation of the cellular respiration processes, such that the keratinocytes forming the hair experience an increase in the cellular respiration through the mitochondria, thereby increasing the energy level that boosts hair growth. The stabilization of the capillary structures (or the hair in general) results in both an improvement in the cellular metabolism and in the ordered growth of tissue.

Moreover, it is also accomplished skin permeability and the electro-osmotic effect discussed above, this making it suitable for simultaneously working with drugs or cosmetics formulated for nourishing or repairing hair deficiencies since they are driven to penetrate during treatment with the system of the invention. Due to this feature, the radiating applicator 11 described above should be airtight in order to prevent these products, liquid by nature, from penetrating into its interior during use.

Figure 5A:
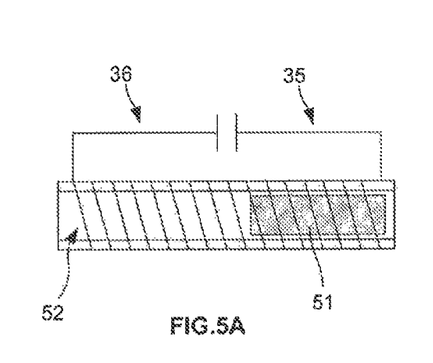
FIG. 5A is a schematic diagram relating to the arrangement of the transformer secondary with respect to the core intended to regulate the operating frequency of system.
Figure 5B:
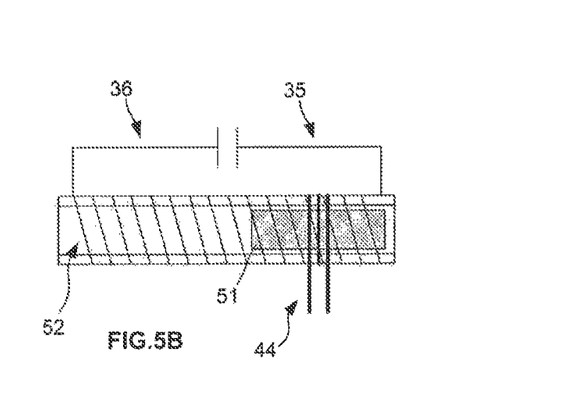
FIG. 5B is a schematic diagram relating to the first arrangement of the transformer primary with respect to the core intended to accomplish control over the radiation pattern generated by the system.
Figure 5C:
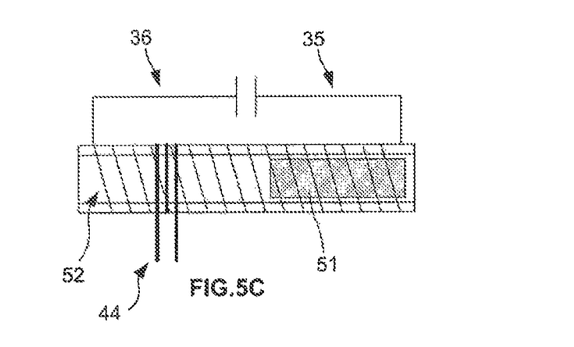
FIG. 5C is a schematic diagram relating to a second arrangement of the transformer primary with respect to the core.

In FIGS. 5B and 5C it can been seen two different arrangements of the coupling (primary winding) 44 in relation to the core 51. Hence, in FIG. 5B the coupling 44 is disposed in relation to the core 51 such that it is attained maximum voltage at the transformer secondary 31. Conversely, in FIG. 5C the coupling is disposed in relation to the core (more specifically, outside the core) so that the current at the secondary is very scarce. In this way, it becomes apparent that it is possible to regulate the radiation pattern of the electric field generated by the radiating elements 35, 36 through the positioning of the coupling in relation to the core. Since FIGS. 5B and 5C show two extreme locations, it is possible to obtain in more intermediate locations than the ones shown the output adjustment of the radiation pattern without the resonant frequency being affected.

Figure 6A:
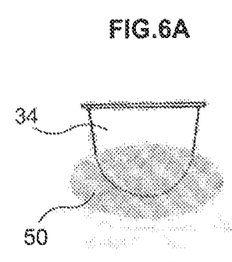
FIG. 6A shows a side view of the head along with the radiation pattern generated approximately on the outer surface thereof.
Figure 6B:
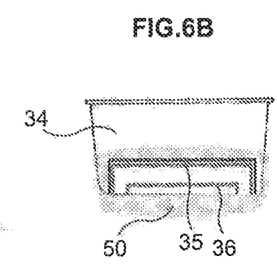
FIG. 6B shows a front view of the head, wherein it can be appreciated the printed circuit board whose conductive tracks constitute the radiating elements, as well as the radiation pattern.
Figure 6C:
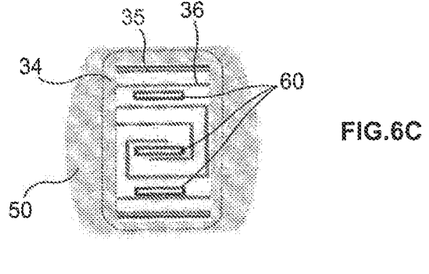
FIG. 6C shows an elevation view of the head, wherein it can be appreciated the printed circuit board disposed therein, as well as the radiation pattern generated.
Figure 6D:
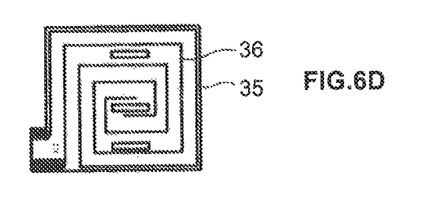
FIG. 6D is a schematic diagram of the printed circuit board that is attached to the inside of the head showing the conductive tracks comprising the radiating elements of the system.

FIGS. 6A and 6D show a possible embodiment of the head 33 that comprises the element 34 made of an insulating material and incorporates the printed circuit board made of a flexible material, which, in turn, incorporates the radiating elements 35, 36 in the form of conductive tracks. In addition, the printed circuit board comprises orifices 60 suitable for attaching the board to the insulating element 34 of the head 33.

The operating frequency of the system of the invention is not significant. For this application the system operates at a frequency range between 100 kHz and 600 Mhz, although it preferably operates at approximately 480 KHz.

As can be seen in FIG. 5A, depending on the location of the area of skin to be treated (in the present preferred embodiment, the system is applied on the scalp), the transformer core 31 is disposed in relation to the resonant circuit in such a way that, during operation, the resonant circuit is in tune.

When the radiating applicator 11 rests on the body a tune change occurs caused by the change of capacitance of the resonant transformer circuit 31, this being corrected through feedback in the generator that changes then its frequency to become tuned and thus maintains its output performance. This change in tune depends to a large extent on the pressure exerted on the tissue on which it rests, on the softness of the tissue, which when adapted, covers a larger contact area, and on the impedance of the tissue in question as well.

In case of resting the applicator on the skull, as it is hard it does not cave in, and besides, since the skull mostly lacks water and fat, it barely loads the output resonant circuit and as a result correction is barely required.

Another important aspect worth noting is that the radiating applicator is trebly insulated from the power supply by means of an input current transformer, an output RF transformer of the generation stage 10 of low-voltage alternating current, and the input RF transformer 31 of the radiating applicator 31, which altogether provides great insulation that makes the applicator very secure and guarantees the absence of leakage currents that may affect the person treated and cause injuries.

Despite that only some of the embodiments and particular instances of the invention have been so far described herein, those skilled in the art will understand that other alternative embodiments and/or uses of the invention, as well as obvious modifications and equivalent elements are also possible. Moreover, the scope of protection of the present invention covers all the possible combinations of the specific embodiments described above. The drawing numerals appearing between brackets in the claims are only intended to try to improve understanding thereof and are not be construed as limiting of the scope of protection of the claims. The scope of the present invention is not to be limited to specific embodiments, it rather has to be only determined by a suitable reading of the accompanying claims.

The invention claimed is:

1. A system for stimulating hair growth in a pre-determined area of skin comprising:
   means for generating high-voltage alternating current;
   means for generating a variable electric field from the high-voltage alternating current generated; and
   means for applying the variable electric field generated on the pre-determined area of skin;
   the means for generating a variable electric field comprising at least two radiating elements; and
   the means for generating high-voltage alternating current comprising a transformer having a primary winding and a core, the primary winding being disposed in relation to the core such that, in operation, the radiating elements generate a variable electric field with a radiation pattern that concentrates its energy near the means for applying the variable electric field.

2. A system according to claim 1, wherein the transformer is resonant and, depending on the location of the pre-determined area of skin in the body, the core is disposed in relation to the resonant circuit such that, in operation, the resonant circuit is in tune.

3. A system according to claim 1, wherein the means for applying the variable electric field are adapted to move across the entire predetermined area of skin such that the same radiation pattern is applied on each of the spots of such pre-determined area of skin.

4. A system according to claim 3 wherein the means for applying the variable electric field comprise a head on which the means for generating an electric field are disposed, and a handle on which the means for generating high-voltage alternating current are disposed.

5. A system according to claim 3 wherein the means for applying the variable electric field comprise a head on which the means for generating a variable electric field are disposed, a housing for the means for generating high-voltage alternating current, and a mechanical system capable of moving at least the head across the entire pre-determined area of skin are disposed.

6. A system according to claim 1, wherein the means for generating high-voltage alternating current generate high-voltage alternating current from low-voltage alternating current and wherein the system also comprises:
   means for generating low-voltage alternating current, and
   means for carrying the low-voltage alternating current so generated to the means for generating high-voltage alternating current.

7. A system according to claim 1, wherein the radiating elements are conductive tracks disposed on a printed circuit board.

8. A system according to claim 7, wherein the printed circuit board is made of a flexible material.

9. A system according to claim 4, wherein the head comprises an element made of an insulating material.

10. A system according to claim 1, wherein the system it operates at a frequency ranging from 100 KHz and 600 Mhz.

11. A system according to claim 1, further comprising means for insulating the system from the power supply.

12. A system according to claim 1, further comprising an element for indicating operation of the system.

13. A system according to claim 1, wherein the element for indicating operation of the system is a red light emitting diode having a wavelength of approximately 630 nm.

* * * * *